(12) United States Patent
Pesaran et al.

(10) Patent No.: US 8,768,449 B2
(45) Date of Patent: Jul. 1, 2014

(54) PROSTHETIC DEVICES AND METHODS AND SYSTEMS RELATED THERETO

(75) Inventors: Bijan Pesaran, Los Angeles, CA (US); Richard A. Andersen, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 427 days.

(21) Appl. No.: 12/828,728

(22) Filed: Jul. 1, 2010

(65) Prior Publication Data

US 2010/0331976 A1    Dec. 30, 2010

Related U.S. Application Data

(62) Division of application No. 11/300,965, filed on Dec. 15, 2005, now Pat. No. 7,797,040.

(60) Provisional application No. 60/636,679, filed on Dec. 16, 2004.

(51) Int. Cl.
*A61B 5/04* (2006.01)

(52) U.S. Cl.
USPC .............................. 600/545; 623/25; 600/544

(58) Field of Classification Search
USPC ..................................... 600/544, 545; 623/25
See application file for complete search history.

(56) References Cited

U.S. PATENT DOCUMENTS

| | | | |
|---|---|---|---|
| 3,841,310 A | 10/1974 | Goldstein | |
| 4,209,860 A | 7/1980 | Graupe | |
| 4,314,379 A | 2/1982 | Tanie et al. | |
| 4,628,933 A | 12/1986 | Michelson | |
| 4,632,116 A | 12/1986 | Rosen et al. | |
| 4,878,913 A | 11/1989 | Aebischer et al. | |
| 4,926,969 A | 5/1990 | Wright et al. | |
| 4,949,726 A | 8/1990 | Hartzell et al. | |
| 5,037,376 A | 8/1991 | Richmond et al. | |
| 5,178,161 A | 1/1993 | Kovacs | |
| 5,215,088 A | 6/1993 | Normann et al. | |
| 5,246,463 A | 9/1993 | Giampapa | |
| 5,314,495 A | 5/1994 | Kovacs | |
| 5,365,939 A | 11/1994 | Ochs | |
| 5,368,041 A | 11/1994 | Shambroom | |

(Continued)

FOREIGN PATENT DOCUMENTS

| | | |
|---|---|---|
| EP | 0 911 061 A2 | 4/1999 |
| WO | 00/09008 A | 2/2000 |

(Continued)

OTHER PUBLICATIONS

Dotsinsky, I.A. et al., Multichannel DC amplifier for a microprocessor electroencephalograph, Medical and Biological Engineering and Computing, May 1, 1991, vol. 29, pp. 324-329.

(Continued)

*Primary Examiner* — Navin Natnithithadha
*Assistant Examiner* — Etsub Berhanu
(74) *Attorney, Agent, or Firm* — Seth D. Levy, Esq.; Nixon Peabody LLP

(57) ABSTRACT

Prosthetic devices, methods and systems are disclosed. Eye position and/or neural activity of a primate are recorded and combined. The combination signal is compared with a predetermined signal. The result of the comparison step is used to actuate the prosthetic device.

16 Claims, 8 Drawing Sheets
(1 of 8 Drawing Sheet(s) Filed in Color)

(56) References Cited

U.S. PATENT DOCUMENTS

| | | | |
|---|---|---|---|
| 5,406,957 A | 4/1995 | Tansey | |
| 5,413,103 A | 5/1995 | Eckhorn | |
| 5,638,826 A | 6/1997 | Wolpaw et al. | |
| 5,687,291 A | 11/1997 | Smyth | |
| 5,692,517 A | 12/1997 | Junker | |
| 5,748,845 A | 5/1998 | Labun et al. | |
| 5,840,040 A | 11/1998 | Altschuler et al. | |
| 5,927,277 A | 7/1999 | Baudino et al. | |
| 6,097,981 A | 8/2000 | Freer | |
| 6,128,527 A | 10/2000 | Howard, III et al. | |
| 6,171,239 B1 | 1/2001 | Humphrey | |
| 6,208,894 B1 | 3/2001 | Schulman et al. | |
| 6,216,119 B1 | 4/2001 | Jannarone | |
| 6,321,110 B1 | 11/2001 | Ito et al. | |
| 6,330,466 B1 | 12/2001 | Hofmann et al. | |
| 6,344,062 B1 | 2/2002 | Abboudi et al. | |
| 6,349,231 B1 | 2/2002 | Musha | |
| 6,516,246 B2 | 2/2003 | Derakhshan | |
| 6,546,378 B1 | 4/2003 | Cook | |
| 6,609,017 B1 | 8/2003 | Shenoy et al. | |
| 6,615,076 B2 | 9/2003 | Mitra et al. | |
| 6,952,687 B2 * | 10/2005 | Andersen et al. | 706/12 |
| 2002/0103429 A1 | 8/2002 | DeCharms | |
| 2002/0107454 A1 | 8/2002 | Collura et al. | |
| 2003/0023319 A1 | 1/2003 | Andersen et al. | |
| 2003/0050569 A1 * | 3/2003 | Shenoy et al. | 600/544 |
| 2003/0139783 A1 | 7/2003 | Kilgore et al. | |

FOREIGN PATENT DOCUMENTS

| | | |
|---|---|---|
| WO | 00/33731 A1 | 6/2000 |
| WO | 01/43635 A1 | 6/2001 |
| WO | 03/000161 A1 | 1/2003 |

OTHER PUBLICATIONS

Ji, J. et al., An implantable CMOS analog signal processor for multiplexed microelectrode recording arrays, IEEE, Feb. 24, 1990, pp. 107-110.

Barer. R. et al. (2000) "E.O.G. Guidance of a Wheelchair Using Spiking Neural Networks," European Symposium on Artificial Neural Networks (ESANN), ISBN 2-930307-00-5, 233-238.

W. Wayt Gibbs, "Mind Readings," Scientific American, vol. 74, No. 1, Jun. 1996. pp. 34-36.

Dr. Richard K. Eisley, "Adaptive Control of Prosthetic Limbs Using Neural Networks," IJCNN Joint Conference on Neural Networks, 1990, pp. II-771-776.

Eisley et al., "Application of Neural Networks to Adaptive Control," 1988.

Snyder, L.H. et al., "Coding of Intention in the Posterior Parietal Cortex," Nature, Mar. 13, 1997, 386:167-70.

Zipser, D and Andersen, RA, "A Back-Propagation Programmed Network that Simulates Response Properties of a Subset of Posterior Parietal Neurons," Nature, Feb. 25, 1988, 331 (6158):679-84.

Clower, DM. et al., "Role of Posterior Parietal Cortex in the Recalibration of Visually Guided Reaching," Nature, Oct. 17, 1996, 383(6601):618-21.

Galleti, C. et al., "Short Communication Arm Movement-related Neurons in the Visual Area V6A of the Macaque Superior Parietal Lobule," European Journal of Neuroscience, Feb. 1997, 9(2):410-3.

Johnson, PB., et al., "Cortical Networks for Visual Reaching: Physiological and Anatomical Organization of Frontal and Parietal Lobe Arm Regions," Cerebral Cortex, Mar./Apr. 1996, 6:102-19.

Lukashin, AV. et al., "A Simulated Actuator Driven by Motor Cortical Signals," NeuroReport, Nov. 1996, 7 (15-17):2597-601.

Lynch, JC, et al., "The Functional Organization of Posterior Parietal Association Cortex," The Behavioral and Brain Sciences, Dec. 1980, 3(4):485-534.

Murthy VN and Fetz EE; Oscillatory Activity in Sensorimotor Cortex of Awake Monkeys: Synchronization of Local Field Potentials and Relation to Behavior; Dec. 1996; Journal of Neurophysiology, vol. 76, No. 6, pp. 3949-3967.

Murthy VN and Fetz EE Synchronization of Neurons During Local Field Potential Oscillations in Sensonmotor Cortex of Awake Monkeys; Dec. 1996; Journal of Neurophysiology, vol. 76, No. 6; pp. 3968-3982.

Cook et al., "Development of a Robotic Device for Facilitating Learning by Children Who Have Severe Disabilities," IEEE Transactions on Neural Systems and Rehabilitation Engineering, Sep. 2002.

Salinas et al. "Transfer of Coded Information from Sensory to Motor Networks," J. Neurosci. 1995, 15:6461:6474.

Batista, A.P. et al. "Reach plan in eye centered coordinates" Science Jul. 9, 1999, vol. 285, pp. 257-260.

Haugland et al. "Artifact free sensory nerve signals obtained from cuff electrodes during electrical stimulation of nearby muscles," IEEE Transactions on Rehabilitation Engineering, vol, 2, No. 1, Mar. 1994, pp. 37-40.

Salinas, E and Abbott, LF "Vector reconstruction from firing rates," Journal of Computational Neuroscience, 1994, 1:89-107.

Zhang, K et al. "Interpreting Neuronal population activity by reconstruction: unified framework with application to hippocampal place cells," Journal of Neurophysiology, Feb. 1998, 79(2):1017-1044.

Brown, EN et al. "A statistical paradigm for neural spike train decoding applied to position prediction from ensemble firing patterns of rat hippocampal place cells," The Journal of Neuroscience, Sep. 15, 1998, 18(18):7411-25.

Buonomano, DV et al. "Cortical plasticity: from synapses to maps," Annual Review of Neuroscience, 1998, 21:49-86.

Colby, CL "Action-oriented spatial reference frames in cortex" Neuron, Jan. 1998, 20:15-24.

Hatsopoulos, NG et al. "Information about movement direction obtained from synchronous activity of motor cortical neurons," Proc. Natl. Acad. Sci. USA, Dec. 1998, 95:15706-11.

Sanes, JN et al. "Oscillations in local field potentials of the primate motor cortex during voluntary movement," May 1993, Proc. Natl. Acad. Sci. USA, vol. 90, pp. 4470-4474.

Smith et al. "An artificial neural network model of certain aspects of fighter pilot cognition," IEEE International Conference on Decision Aiding for Complex Systems, Oct. 13-16, 1991.

Buneo, CA et al. (2002). "Direct visuomotor transformations for reaching," Nature 416:632-636.

Cohen, YE et al. (2002). "Comparison of neural activity preceding reaches to auditory and visual stimuli in the parietal reach region," NeuroReport 13:891-894.

Grunewald, A et al. (2002) "Neural correlates of structure-from-motion perception in macaque V1 and MT," J. Neurosci. 22:6195-6207.

Pesaran, B el al. (2002) "Temporal structure in neuronal activity during working memory in Macaque parietal cortex," Nature Neuroscience 5: 805-811.

Sabes, PN et al. (2002) "The parietal representation of object-based saccades," J. Neurophysiol. 88: 1815-1829.

Shenoy, KV et al. (2002) "Pursuit speed compensation in cortical area MSTd," J. Neurophysiol. 88:2630-2647.

Sugihara, H et al. (2002) "Responses of MSTd neurons to simulated 3D-orientation of rotating planes," J. Neurophysiol. 87:273-285.

Andersen, RA et al. (2002) "Intentional maps in posterior parietal cortex," Ann.Rev.Neurosci 25:189-200.

Cohen, YE et al. (2002) "A common reference frame for movement plans in the posterior parietal cortex," Nature Review Neuroscience 3:553-562.

Scherberger, H et al. (2002) "Sensorimotor transformation in the posterior parietal cortex," The Visual Neurosciences, Cambridge, MA, MIT Press, 1324-1336.

Jarvis, MR et al. "Sampling properties of the spectrum and coherency of sequences of action potentials," Neural Computation, 13(4):717-749 Apr. 2001.

Li, C-S et al. (2001) "Inactivation of macaque area LIP delays initiation of the second saccade from contralesional eye positions in a double-saccade task," Exp. Brain Res. 137:45-57.

Cohen, YE et al. (2000) "Reaches to sounds encoded in an eye-centered reference frame," Neuron 27:647-652.

Desouza, JFX et al. (2000) "Eye position signal modulates a human parietal pointing region," J. Neurosci. 20:5835-5840.

(56) References Cited

OTHER PUBLICATIONS

Snyder, LH et al. (2000) "Saccade-related activity in the parietal reach region," J. Neurophysiol. 83:1099-1102.

Xing, J et al. (2000) "Models of posterior parietal cortex which perform multimodal integration and represent space in several coordinate frames," J. Cognitive Neurosci. 12:601-614.

Xing, J et al. (2000) "The memory activity of LIP neurons in sequential eye movements simulated with neural networks," J. Neurophysiol. 84:651-665.

Snyder, LH et al. (2000) "Intention-related activity in the posterior parietal cortex: a review," Vision Res. 40:1433-1441.

Branchaud, EA et al. "A miniature robot that autonomously optimizes and maintains extracellular neural action potential recordings," Proceedings of the 2005 Int'l Conf. Robotics and Automation.

Takahashi, M et al. Neural Network for Human Cognitive State Estimation IEEE International Conference on Advanced Robotic System and the Real World, Sep. 12-16, 1994.

Andersen, RA et al. (2003) "Sensorimotor integration in posterior parietal cortex," Advances in Neurology vol. 93—The Parietal Lobes, Siegal, AM, Andersen, RA; Freund H and Spencer DD, Philadelphia, Lippincott Williams & Wilkins, 159-179.

Ariff, G. et al., A Real-Time State Predictor in Motor Control: Study of Saccadic Eye Movements during Unseen Reaching Movements, The Journal of Neuroscience, Sep. 1, 2002, 22(17):7721-7729.

Ballard, D.H. et al., Spatio-temporal organization of behavior, Spatial Vision, (2000), 13(2,3):321-333.

Barraclough, D.J. et al., Prefrontal cortex and decision making in a mixed-strategy game, Nature Neuroscience, Apr. 2004, 7(4)L404-410.

Batista, A.P. et al., Reach Plans in eye-Centered Coordinates, Science, Jul. 9, 1999, vol. 285:257-260.

Cisek, P. et al., Modest Gaze-Related Discharge Modulation in Monkey Dorsal Premotor Cortex During a Reaching Task Performed With Free Fixation, J. Neurophysiol, 2002, 88:1064-1072.

Fisk, J.D. et al., The organization of eye and limb movements during unrestricted reaching to targets in contralateral and ipsilateral visual space, Exp Brain Res, 1985, 60:159-178.

Gnadt, J.W. et al., Memory related motor planning activity in posterior parietal cortex of macaque, Exp Brain Res, 1988, 70:216-220.

Hayhoe, M.M. et al., Coordination of Eye and Hand Movements in a Normal Visual Environment, Investigative Ophthalmology & Visual Science, 1999, vol. 40, S380, Abstract.

Hayhoe, M.M. et al., Visual memory and motor planning in a natural task, Journal of Vision, 2003, 3:49-63.

Johansson, R.S. et al., Eye-Hand Coordination in Object Manipulation, The Journal of Neuroscience, Sep. 1, 2001, 21(17):6917-6932.

Johnson, P.B. et al., Cortical Networks for Visual Reaching: Physiological and Anatomical Organization of Frontal and Parietal Lobe Arm Regions, Cerebral Cortex, Mar./Apr. 1996, 6:102-119.

Land, M.F. et al., From eye movements to actions: how batsmen hit the ball, Nature Neuroscience, Dec. 2000, 3(12)1340-1345.

Land, M.F. et al., In what ways do eye movements contribute to everyday activities?, Vision Research, 2001, 41:3559-3565.

Land, M.F. et al., Where we look when we steer, Nature, Jun. 30, 1994, 369:742-744.

Lewis, J.W. et al., Corticocortical Connections of Visual, Sensorimotor, and Multimodal Processing Areas in the Parietal Lobe of the Macaque Monkey, The Journal of Comparative Neurology, 2000, 428:112-137.

Logothetis, N.K. et al., Functional imaging of the monkey brain, Nature Neuroscience, Jun. 1999, 2(6):555-562.

Logothetis, N.K., The neural basis of the blood-oxygen-level-dependent functional magnetic resonance imaging signal, Phil. Trans, R. Soc. Lond. B, 2002, 357:1003-1037.

Mitzdorf, U., Current Source-Density Method and Application in Cat Cerebral Cortex: Investigation of Evoked Potentials and EEG Phenomena, Physiological Reviews, Jan. 1985, 65(1):37-100.

Musallam, S. et al., Cognitive Control Signals for Neural Prosthetics, Science, Jul. 2004, 305:258-262.

Pesaran, B. et al., Temporal structure in neuronal activity during working memory in macaque parietal cortex, Nature Neuroscience, Aug. 2002, 5(8):805-811.

Platt, M.L., Neural correlates of decisions, Current Opinion in Neurobiology, 2002, 12:141-148.

Platt, M.L. et al., Neural correlates of decision variables in parietal cortex, Nature, Jul. 15, 1999, 400:233-238.

Scherberger, H. et al., Cortical Local Field Potential Encodes Movement Intentions in the Posterior Parietal Cortex, Neuron, Apr. 21, 2005, 46:347-354.

Scherberger, H. et al., Magnetic resonance image-guided implantation of chronic recording electrodes in the macaque intraparietal sulcus, Journal of Neuroscience Methods, 2003, 130:1-8.

Scherberger, H. et al., Target Selection for Reaching and Saccades Share a Similar Behavioral Reference Frame in the Macaque, J Neurophysiol, 2003, 89:1456-1466.

Serruya, M.D. et al., Instant neural control of a movement signal, Nature, Mar. 14, 2002, 416:141-142.

Shlmojo, S. et al., Gaze bial both reflects and influences preference, Nature Neuroscience, Dec. 2003, 6(12):1317-1322.

Sugrue, L.P. et al., Matching Behavior and the Representation of Value in the Parietal Cortex, Science, Jun. 18, 2004, 304:1182-1787.

Taylor, D.M. et al., Direct Cortical Control of 3D Neuroprosthetic Devices, Science, Jun. 7, 2002, 296:1829-1832.

Donoghue, JP et al., "Neural discharge and local field potential oscillations in primate motor cortex during voluntary movements," J. Neurophysiol 79:159-173, 1998.

Batista, AP and RA Anderson, "The Parietal Reach Region Codes the Next Planned Movement in a Sequential Reach Task," J. Neurophysiol 85:539-544, 2001.

Crowell, JA et al. "Pursuit compensation during self-motion," Perception 30(12) 1465-88, 2001.

Dubowitz, DJ et al., "Direct comparison of visual cortex activation in human and non-human primates using functional magnetic resonance imaging," J. Neurosci. Methods 107:71-80, 2001.

Dubowitz, DJ et al., "Enhancing fMRI contrast in awake-behaving primates using intravascular magnetite dextran nanoparticles," NeuroReport 12:2335-2340, 2001.

Carmena, JM et al., "Learning to Control a Brain-Machine Interface for Reaching and Grasping by Primates," PLoS Biology 1(2) :193-208, 2003.

Scherberger, H et al. (2005). "Cortical Local Field Potential Encodes Movement Intentions in the Posterior Parietal Cortex." Neuron. 46:347-354.

Campos, M et al. (2005). "The Supplementary Motor Area Encodes Reward Expectancy in Eye Movement Tasks." J. Neurophysiol. 94:1325-1335.

Rizzuto, D et al. (2005). "Spatial Selectivity in Human Ventrolateral Prefrontal Cortex." Nature Neuroscience. 8:4:415-417.

Cham, JG et al. (2005). "Semi-chronic Motorized Microdrive and Control Algorithm for Autonomously Isolating and Maintaining Optimal Extracellular Action Potentials." J. Neurophysiol. 93:570-579, 2005.

Pang, C et al. (2005). "A New Multi-Site Probe Array with Monolithically Integrated Parylene Flexible Cable for Neural Prostheses." Proceedings of the 27th Annual International Conference of the IEEE Engineering in Medicine and Biology Society.

Andersen, RA et al. (2005). "Cognitive Based Neural Prosthetics." Proceedings of the 2005 Intl. Conf. Robotics and Automation.

Buneo CA et al. "The posterior parietal cortex: Sensorimotor interface for the planning and online control of visually guided movements," Neuropsychologia. Nov. 18, 2005.

Andersen, RA et al. "Selecting the signals for a brain-machine interface," Curr Opin Neurobiol. Dec. 2004; 14(6):720-6.

Andersen, RA et al. "Cognitive neural prosthetics," Trends Cogn Sci Nov. 2004; 8(11):486-93.

Buneo, CA et al. "Properties of spike train spectra in two parietal reach areas," Exp Brain Res. Nov. 2003: 153(2):134-9. Epub Aug. 28, 2003.

(56) References Cited

OTHER PUBLICATIONS

Pesaran, B et al. "Dorsal premotor neurons encode the relative position of the hand, eye, and goal during reach planning." Neuron. Jul. 6, 2006; 51(1):125-34.

Quiroga, QR et al. "Movement intention is better predicted than attention in the posterior parietal cortex" J. Neurosci. Mar. 29, 2006; 26(13):3615-20.

Musallam, S et al. "Cognitive control signals for neural prosthetics." Science Jul. 9, 2004; 305 (5681):258-62.

Corneil, BD et al. "Dorsal neck muscle vibration induces upward shifts in the endpoints of memory-guided saccades in monkeys." J Neurophysiol. Jul. 2004; 92(1):553-66. Epub Mar 3, 2004.

Scherberger, H et al. "Magnetic resonance image-guided implantation of chronic recording electrodes in the macaque intraparietal sulcus." J Neurosci Methods Nov. 30, 2003; 130(1):1-8.

Connolly, JD et al. "FMRI evidence for a 'parietal reach region' in the human brain." Exp Brain Res. Nov. 2003; 153 (2):140-5. Epub Sep. 4, 2003.

Andersen, RA et al. (2004) "Recording Advances for Neural Prosthetics," Proceedings of the 26th Annual International Conference of the IEEE IMBS, San Francisco, CA, USA, Sep. 1-5, 2004, 5352-5355.

Engenious. By Pure Thought Alone: The Development of the First Cognitive Neural Prosthesis by Burdick, JW and Andersen, RA, Pasadena, CA, Caltech, 2004.

Andersen, R et al. (2004) "Sensorimotor Transformations in the Posterior Parietal Cortex," The Cognitive Neurosciences III, Ed. MS Gazzaniga, Cambridge, MA:MIT P:2004, 463-474.

Cohen, YE et al. (2004). "Multimodal spatial representations in the primate parietal lobe," Crossmodal Space and Crossmodal Attention, J. Driver and C. Spence (Eds.) pp. 99-122, Oxford University Press.

Cohen, YE et al. (2004). "Multisensory representations of space in the posterior parietal cortex," In: Handbook of Multisensory Integration, G, Calvert, C. Spence, and B. Stein (Eds.), pp. 463-479, MIT Press, Cambridge, MA.

Mojarradi, M et al. (2003). "A miniaturized neuroprosthesis suitable for implants into the brain," IIEE Transactions on Neural Systems and Rehabilitation Engineering 11:1534-4320.

Nishida, S et al. (2003) "Gaze modulation of visual aftereffects," Vision Research 43:639-649.

Scherberger, H et al. (2003) "Target selection for reaching and saccades share a similar behavioral reference frame in the macaque," J. Neurophysiol. 89:1456-1466.

Shenoy, KV et al. (2003). "Neural prosthetic control signals from plan activity," NeuroReport 14:591-597.

* cited by examiner

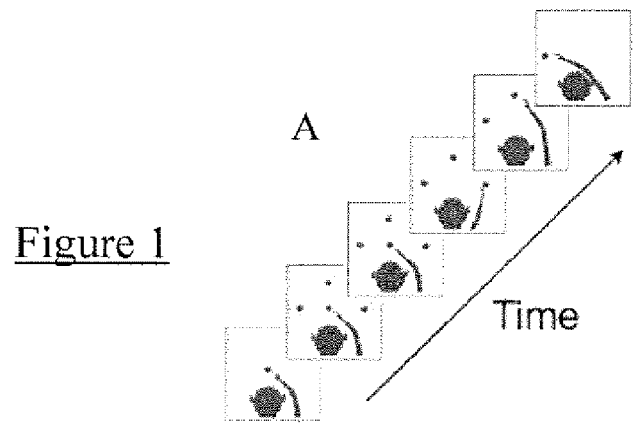
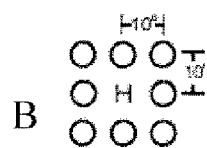
Figure 1
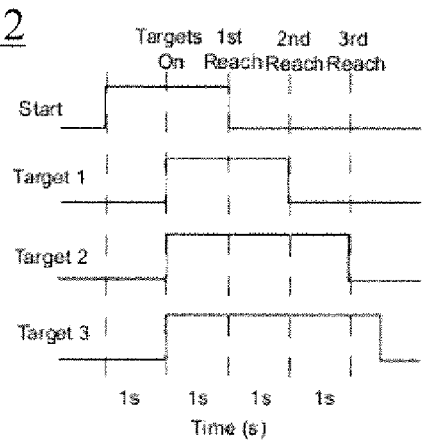
Figure 2

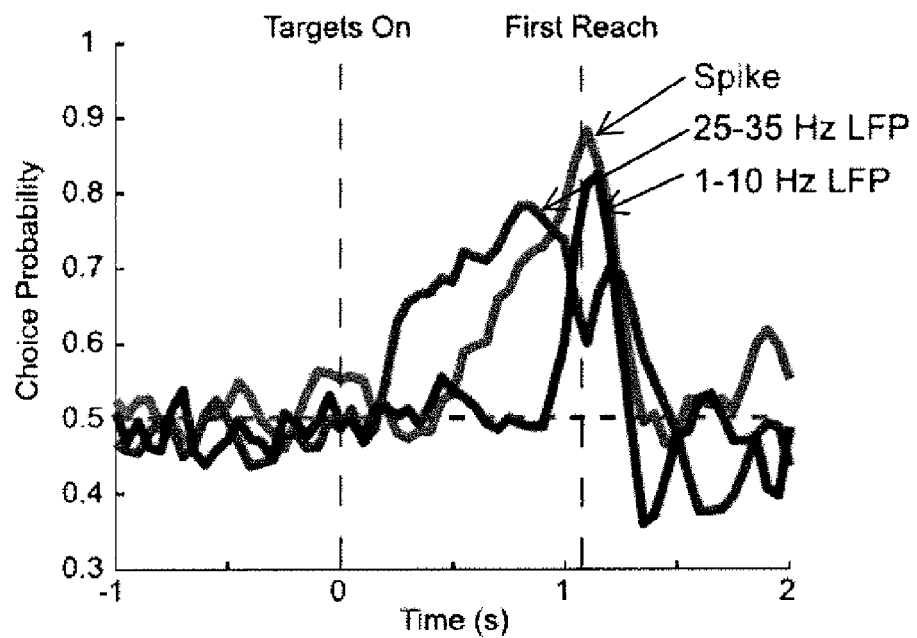
Figure 12 Single site
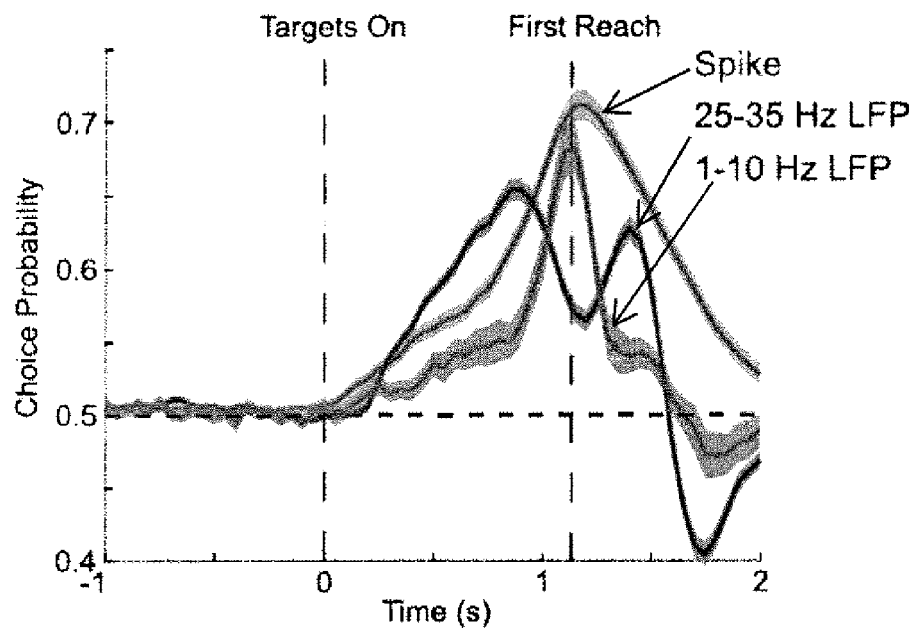
Figure 13 Population average

PROSTHETIC DEVICES AND METHODS AND SYSTEMS RELATED THERETO

CROSS REFERENCE TO RELATED APPLICATIONS

The present application claims the benefit of priority under 35 U.S.C. §121 as a divisional of Application Serial No. 11/300,965, filed Dec. 15, 2005, currently pending, which claims the benefit of provisional application 60/636,679 for "Neural Prosthetic Combining Eye Position Information and Neural Activity" filed on Dec. 16, 2004, which is incorporated herein by reference in its entirety.

FEDERAL SUPPORT

This invention was made with U.S. Government support under DARPA grant no. MDA972-00-1-0029 and National Institute of Health grant nos. R01 EY005522 and R01 EY013337. The U.S. Government has certain rights in this invention.

BACKGROUND

1. Field

The present disclosure relates to control methods and systems applied to prosthetic devices and to methods and systems that incorporate and/or investigate neural bases of behavior.

2. Related Art

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Eye movements may be broadly categorized into those that are voluntary and those that are involuntary. Among other things, involuntary eye movements compensate for head movement; account for a moving background behind an object on which vision is focused; and act in a reflexive manner to external stimuli. At least certain voluntary eye movements, on the other hand, are known to relate to motor coordination and other behavioral attributes and processes.

Most voluntary eye movements are properly classified as saccades, as smooth pursuit eye movement, or as vergence movement. Saccades and smooth pursuit eye movement relate to two dimensions in a visual field (i.e., the x- and y-axis in a coordinate system), while vergence movement accounts for depth (i.e., the z-axis). More particularly, saccades are eye movements in which the eyes rapidly jump from one point to another (e.g., from one word to the next while reading or around a room when searching for an object); smooth pursuit eye movement involves eye movements that smoothly track slowly moving objects in the visual field; and vergence movement—a relatively slow eye movement—occurs when both eyes coordinate to form an angle in a particular gaze direction (e.g., to focus on an object at a particular depth in the visual field). Voluntary eye movements act in concert with other physiological functions, such as motor function and psychological features of perception, to coordinate behavior. Based on the coordinated nature of behavior, measurements of voluntary eye movement as a function of time enable the prediction of movement.

Eyes move so quickly and easily that voluntary eye movements, generally, and saccadic eye movements, in particular, are a central feature of primates' natural behavior. Voluntary eye movements are not only crucial for visual perception, but they also play an important role in motor control and provide visual guidance for action. Indeed, orchestration of hand and eye movements as we look and reach occurs frequently in natural behavior (D. H. Ballard et al., *Spatio-temporal organization of behavior, Spatial Vision*, 13:321-333 (2000); Land, M. F. & Hayhoe, M., *In what ways do eye movements contribute to everyday activities?, Vision Res.*, 41:3559-3565 (2001)). In addition to these sensory and motor roles, voluntary eye movements also participate in higher cognitive processes. They are involved in shifting the locus of spatial attention and both reflect and influence preferences and decisions (H. Scherberger et al., *Target selection for reaching and saccades share a similar behavioral reference frame in the macaque, J. Neurophysiol.*, 89:1456-1466 (2003)). Studies of eye movements in humans under naturalistic conditions reveal saccades are part of strategies to limit the cognitive demands of a task (Land, M. F. & Hayhoe, M., *In what ways do eye movements contribute to everyday activities?, Vision Res.*, 41:3559-3565 (2001); M. M. Hayhoe et al., *Visual memory and motor planning in a natural task, J. Vis.*, 3:49-63 (2003); H. Scherberger et al., *Target selection for reaching and saccades share a similar behavioral reference frame in the macaque, J. Neurophysiol.*, 89:1456-1466 (2003)). Despite this multiplicity of roles in higher brain function, however, there has been relatively little physiological work studying eye movements when the eyes are free to move. In fact, most studies of eye movements have employed tasks with explicit instructions that require controlled fixation. While allowing a degree of experimental tractability, this approach is not well-suited for understanding voluntary eye movements, such as saccades, and the underlying brain mechanisms during natural behaviors.

Another hallmark of natural behavior is decision-making. A body of work now implicates a number of cortical areas in the neural basis of decision-makings; in particular, sensory-motor areas in the parietal cortex having strong anatomical connections with each other and with areas in the frontal cortex. Neuronal activity in these distributed networks can be divided into two distinct classes: spiking and local field potential (LFP) activity. Spiking is due to action potentials from individual cells while field potentials reflect synaptic activity and return currents from a population of cells near the tip of the recording electrode (U. Mitzdorf, *Current source-density method and application in cat cerebral cortex: investigation of evoked potentials and EEG phenomena, Physiol. Rev.*, 65:37-100 (1985)). Recent work studying area LIP and PRR in the posterior parietal cortex shows that LFP activity as well as spiking reflects information processing (Scherberger, H., Jarvis, M. R., and Andersen, R. A., *Cortical Local Field Potential Encodes Movement Intentions in the Posterior Parietal Cortex, Neuron*, 46:347-354 (2005)). Despite the results showing that natural behavior critically depends on higher cortical function, there has been little direct work on this at a physiological level.

Recent work in multiple institutions has demonstrated the feasibility of a neural prosthetic based on cortical recordings. Some of this work focused on decoding motor variables, such as movement trajectory (M. D. Serruya et al., *Instant neural control of a movement signal, Nature*, 416:141-142 (2002); J. M. Carmena et al., *Learning to control a brain-machine interface for reaching and grasping by primates, Plos Biol.*, 1:193-208 (2003); D. M. Taylor et al., *Direct cortical control of 3D neuroprosthetic devices, Science*, 296:1829-1832 (2002)), while other work decodes cognitive variables such as movement goals and expected value (S. Musallam et al., *Cognitive control signals for neural prosthetics, Science,* 305:258-262 (2004)). But, whether coordinated eye movements could also be used for this application was heretofore an open question.

There is therefore a need in the art for systems and methods that incorporate measurements of eye movement—and particularly, voluntary eye movement—in the mechanisms that control neural prosthetics, either alone or in combination with cortical recordings relating to other functions, such as decision-making.

SUMMARY

The following embodiments and aspects thereof are described and illustrated in conjunction with systems and methods which are meant to be exemplary and illustrative, not limiting in scope.

Subjects suitable for use in connection with various embodiments of the invention include any animals that make eye movements, such as mammals, which, as used herein, refers to any member of the class Mammalia, including, without limitation, humans and non-human primates.

According to a first aspect, a method to control spatial positioning of a prosthetic device of a subject is disclosed, the prosthetic device being able to assume multiple spatial positions upon input from the subject.

The method comprises: directly and/or indirectly recording eye position of the subject to produce an eye position signal; recording neural activity relating to a motor, cognitive and/or other function of the subject to produce a neural activity signal; combining the eye position signal and the neural activity signal to provide a recorded behavioral pattern; comparing the recorded behavioral pattern with at least one predetermined behavioral pattern to identify a matching predetermined behavioral pattern, the at least one predetermined behavioral pattern associated with at least one predetermined spatial position of the prosthetic device; and positioning the prosthetic device in a spatial position associated with the matching predetermined behavioral pattern.

According to a second aspect, a method to control spatial positioning of a prosthetic device of a subject is disclosed, the prosthetic device being able to assume multiple spatial positions upon input from the subject.

The method comprises: directly and/or indirectly recording eye position of the subject to produce an eye position signal; comparing the eye position signal with at least one predetermined eye position signal to identify a matching predetermined eye position signal, the at least one predetermined eye position signal associated with at least one predetermined spatial position of the prosthetic device; and positioning the prosthetic device in the spatial position associated with the matching predetermined eye position signal.

According to a third aspect, a prosthetic device able to assume a spatial position on input of a subject is disclosed, the prosthetic device comprising: means for directly and/or indirectly recording eye position of the subject to produce an eye position signal; means for recording the neural activity relating to a motor, cognitive and/or other function of the subject to produce a neural activity signal; means for combining the eye position signal and the neural activity signal to produce a recorded behavioral pattern; means for storing at least one predetermined behavioral pattern, the at least one predetermined behavioral pattern associated with at least one spatial positioning of the prosthetic device; means for comparing the recorded behavioral pattern and the at least one predetermined behavioral pattern to identify a matching predetermined behavioral pattern; and means for positioning the prosthetic device in a spatial position associated with the matching predetermined behavioral pattern.

According to a fourth aspect, a prosthetic device able to assume a spatial position on input of a subject is disclosed, the prosthetic device comprising: means for directly and/or indirectly recording eye position of the subject to produce an eye position signal; means for comparing the eye position signal with at least one predetermined eye position signal to identify a matching predetermined eye position signal, the at least one predetermined eye position signal associated with at least one predetermined spatial position of the prosthetic device; and means for positioning the prosthetic device in a spatial position associated with the matching predetermined eye position signal.

According to a fifth aspect, a prosthetic device able to assume a spatial position on input of a subject is disclosed, the prosthetic device comprising: an eye position recorder for directly and/or indirectly recording eye position of the subject to produce an eye position signal; a neural activity recorder for recording neural activity relating to a motor, cognitive and/or other function of the subject and to produce a neural activity signal; a component for combining the eye position signal and the neural activity signal to produce a recorded behavioral pattern; a storage mechanism for storing at least one predetermined behavioral pattern, the at least one predetermined behavioral pattern associated with at least one spatial positioning of the prosthetic device; a processor for comparing the recorded behavioral pattern and the at least one predetermined behavioral pattern to identify a matching predetermined behavioral pattern; and a control system for positioning the prosthetic device in a spatial position associated with the matching predetermined behavioral pattern.

According to a sixth aspect, a prosthetic device able to assume a spatial position on input of a subject is disclosed, the prosthetic device comprising: an eye position recorder for directly and/or indirectly recording eye position of the subject to produce an eye position signal; a processor for comparing the recorded behavioral pattern and at least one predetermined behavioral pattern to identify a matching predetermined behavioral pattern; and a control system for positioning the prosthetic device in a spatial position associated with the matching predetermined behavioral pattern.

According to a seventh aspect, a method to investigate neural basis of a natural behavior in subjects is disclosed. The method comprises: providing at least one subject; providing a behavioral task, the behavioral task simulating a natural behavior in subjects; recording the behavior of the at least one subject during the behavioral task; directly and/or indirectly recording the eye movement of the at least one subject during the behavioral task; recording the neural activity relating to a motor, cognitive and/or other function of the at least one subject during the behavioral task; and combining the recorded behavior, the recorded eye movement and the recorded neural activity to identify a pattern of recorded eye movement and neural activity characterizing the natural behavior.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The above-mentioned features and aspects of the present disclosure will become more apparent with reference to the following description taken in conjunction with the accompanying drawings wherein like reference numerals denote like elements. It is intended that the embodiments and figures disclosed herein are to be considered illustrative rather than restrictive.

FIG. 1 shows a schematic representation of a behavioral task in accordance with an embodiment of the invention. Panel A shows six sections, disposed along an arrow representing time flow during the task and illustrating different moments of the task; in each section a monkey is shown, reaching one of three visually identical targets (asterisks) located on a touch-screen in front of the monkey. Panel B shows a square grid illustrating the possible location of the targets in the touch-screen of panel A, the square grid composed of eight posts spaced by 10° and disposed around the monkey's hand position (H) at the start of the task.

FIG. 2 shows a histogram illustrating the timing of behavioral events registered in the task of FIG. 1 in accordance with an embodiment of the invention. The x-axis shows the time in seconds; the y-axis shows the target reached by the monkey at the first second or third reach. Note that second and third reaches were only made if the reward was not earned for the first reach.

FIG. 12 shows a diagram illustrating single subject choice probabilities from ROC analysis using spiking, 1-10 Hz LFP activity and 25-35 Hz LFP activity in accordance with an embodiment of the invention. The x-axis shows the time expressed in seconds; the y-axis shows the choice probability.

FIG. 13 shows a diagram illustrating the population average choice probabilities from ROC analysis using spiking, 1-10 Hz LFP activity and 25-35 Hz LFP activity in accordance with an embodiment of the invention. The x-axis shows the time expressed in seconds; the y-axis shows the choice probability.

DETAILED DESCRIPTION

Figure 3:
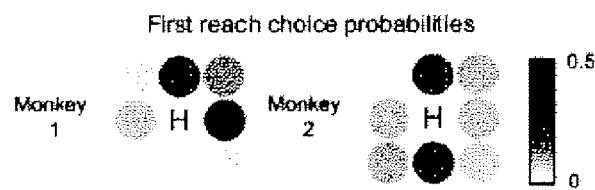
FIG. 3 shows a schematic representation of the first reach choice probabilities for two monkeys subjected to the behavioral task illustrated in FIG. 1 in accordance with an embodiment of the invention. The location of the circle shows the target position with respect to the initial hand position (H). The darkness of the circle illustrates the probability measured according to the scale reported as a bar on the right, wherein white color indicates 0 and the black color indicates 0.5.

The systems and methods of the present invention are based on the incorporation of measurements of eye movement into, among other things, control mechanisms for neural prosthetics. As further described herein, measurements of eye movement or inferred eye movement can act as a surrogate for or supplement to other neural signals recognizing movement. In various embodiments of the present invention, measurements of eye movement may be combined with measurements of neural activity relating to motor, cognitive, or other functions to enhance and/or refine the control, operation, efficiency and/or accuracy of neural prosthetics.

The various embodiments of this invention may be used with any animals that make eye movements, such as mammals, which, as used herein, refers to any member of the class Mammalia, including, without limitation, humans and non-human primates such as chimpanzees, and other apes and monkey species; farm animals such as cattle, sheep, pigs, goats and horses; domestic mammals such as dogs and cats; laboratory animals including rodents such as mice, rats and guinea pigs, and the like.

Measurement of eye movement can be accomplished directly or indirectly via a number of techniques. In one embodiment of the present invention, eye movement may be directly measured with eye video tracking technology (e.g., using a bright light source to produce Purkinje images and tracking the relative movements of these images, and/or combining a video image with computer software to calculate the position of the pupil and its center); with scleral search coils (i.e., small coils of wire embedded in a contact lens are inserted into the eye such that horizontal, vertical and/or tortional eye movement can be measured based on an external magnetic field); and/or through a measurement of eye muscle activity via electrooculography (i.e., measuring small voltages recorded from the region around the eyes that vary with change in eye position) or infrared oculography (i.e., directing an infrared light source at the eye and correlating eye position with the amount of light reflected back to a fixed detector). Head position signals can be used with eye position signals to measure the direction of gaze when saccades are produced by combined eye and head movements. Similar techniques to those used for measuring eye position can be used for measuring head position.

Detection of saccades, more specifically, can be performed by first establishing a velocity threshold (e.g., 50°/sec., 100°/sec., etc.). When the rate of eye movement reaches or exceeds this threshold, a saccadic event is determined to have occurred. Then, one can determine the nature and extent of the saccade by identifying its beginning and end points. This may be accomplished by establishing a second velocity threshold (e.g., 20°/sec.) that corresponds to the initiation and termination of a saccade (i.e., when the eye velocity exceeds the second velocity threshold immediately prior to exceeding the first velocity threshold, and when the eye velocity drops below the second velocity threshold immediately following exceeding the first velocity threshold).

Alternatively or in addition to direct measurement of eye movement, eye movement may be measured indirectly by a number of techniques in accordance with an embodiment of the invention. Certain parts of the brain produce neural signals relating to eye movement (e.g., the lateral intraparietal area of the intraparietal sulcus, the frontal eye fields, the supplementary eye fields, the superior colliculus, the medial parietal area, the dorsal and ventral prefrontal cortex, the dorsal premotor cortex, the parietal reach region, etc.). Neural activity measured in one or more of these locations may be associated with eye movement, by statistical inference or otherwise. This provides an indirect measurement of eye movement.

Still other parts of the brain produce neural signals that reflect eye position, although they are not themselves responsible for eye movement. By way of example, the visual cortex produces, among other things, signals relating to the intensity of light on the retina. Thus, if the position of an external light source in the visual field is known, then eye movement may be indirectly measured based on the location on the retina of, for instance, greatest relative light intensity. It is considered to be within the scope of the present invention to implement similar, indirect techniques involving other areas of the brain and other correlations of brain function to eye movement.

Furthermore, neurons in many areas of the brain, including those mentioned above which carry saccade signals, also carry a signal directly related to eye position; that is the location of the eyes in the orbits (R. A. Andersen at al., *Neurons of area 7 activated by both visual stimuli and oculomotor behavior*, Exp. Brain Res., 67:316-322 (1987)). These signals may be derived from the integration of the saccade command or by way of proprioceptive sensors in the eye muscles. These signals can be used to indicate the direction of the subject's gaze. Other neurons carry both visual signals related to the location of an object's projection on the retina and the position of the eyes in the orbits. These signals can add linearly or combine multiplicatively, or a combination of addition and multiplication. This interaction produces "gain fields" that can be used to determine the direction of gaze and the location of targets with respect to the head (R. A. Andersen et al., *The encoding of spatial location by posterior parietal neurons*, Science, 230:456-458 (1985); Zipser, D., and Andersen, R. A., *A back propagation programmed network that simulates response properties of a subset of posterior parietal neurons*, Nature, 331:679-684 (1988)). Other neurons carry gaze direction signals or have gaze direction gain fields (P. R. Brotchie et al., *Head position signals used by parietal neurons to encode locations of visual stimuli*, Nature, 375:232-235 (1995)). The gaze direction signal is a linear or quasi-linear sum of an eye position signal and a head position signal. All of the cases above can be used to extract eye and gaze direction for the described invention.

Thus, as used herein, and in connection with various embodiments of the present invention, measurements of "eye position" may take into account eye position, head position, gaze direction, gain fields and/or other, similar features that relate to eye movement, position, and orientation. Therefore, measurements of eye and head movement as well as gaze and orbital direction may be integrated to provide a single measurement of "eye position." Moreover, as used herein, an "eye position signal" produced by such measurements may thus include components of eye movement, head movement, gaze, etc. The eye position signal, which integrates this variety of measurements relating to eye position, may thus be used to control or to supplement the control of a neural prosthetic device as described in connection with alternate embodiments of the present invention.

Any one or more of the aforementioned indirect measurements of eye movement, head movement and gaze direction can be obtained using conventional techniques, as will be readily appreciated by those of skill in the art, such as spike measurements or measurements of LFP. Various devices and methodologies may be used to accomplish this feature of the invention, including, without limitation, the use of electrodes, optical measurements, and/or other mechanisms for detecting and quantifying brain function. These may be implemented in connection with computer software and/or other computational devices and machinery, as illustrated in the ensuing Examples.

Regarding spike measurements, in one embodiment of the present invention, an electrode or array of electrodes may be implanted into the region of interest in a subject's brain and used to measure the signals produced by the firing of a single unit (SU) (i.e., a neuron) in the vicinity of an electrode. The SU signal may contain a high frequency component. This component may contain spike-distinct events that exceed a threshold value for a certain amount of time (e.g., a millisecond). Spikes may be extracted from the signal and sorted using known spike sorting methods.

However, measuring SU activity with a chronic implant may be difficult because the SU signal may be difficult to isolate. An electrode may be in the vicinity of more than one neuron, and measuring the activity of a target neuron may be affected by the activity of an adjacent neuron(s). The implant may shift position in the brain after implantation, thereby changing the proximity of an electrode to recorded neurons over time. Also, the sensitivity of a chronically implanted electrode to SU activity may degrade over time.

Thus, in an alternate embodiment of the present invention, LFP may be measured. LFP is an extracellular measurement that represents the aggregate activity of a population of neurons. Information provided by the temporal structure of the LFP of neural activity is believed to correlate to that provided by SU activity. Unlike SU activity, measuring LFP activity does not require isolating the activity of a SU. Accordingly, it may be advantageous to use LFP activity instead of, or in conjunction with, SU activity to obtain an indirect measurement of a subject's eye movement.

The activity of neurons in a subject's brain may be recorded with an implant. The implant may include an array of electrodes that measure the action potential (SU) and/or extracellular potential (LFP) of cells in their vicinity. In one embodiment, micro-electro-mechanical (MEMS) technology may be used to prepare a movable electrode array implant. In alternate embodiments, the neural activity may be measured in forms other than electrical activity. These include, for example, optical or chemical changes, or changes in blood flow that may be measured by suitable measuring devices.

Neural activity measured with an implant may be amplified in one or more amplifier stages and digitized by an analog-to-digital converter. In an embodiment, multiple implants may be used. Recordings may be made from multiple sites in a brain area, each of which conveys different information. The signals recorded from different implants may be conveyed on multiple channels. By way of example, a system of the invention may record signals relating to direct and/or indirect measurements of eye movement from one or more areas of the brain simultaneously.

Therefore, spike measurement, measurement of LFP, or other known techniques such as the optical measure of neural activity using voltage sensitive dyes, metabolite sensitive (such as calcium release) dyes or activity dependent blood flow changes, may be used to collect neural signaling information relating to eye movement, and, thus, to indirectly measure eye movement. This may be performed alone or in combination with direct measurement of eye movement.

In one embodiment of the invention, a direct and/or indirect measurement of eye movement, either alone or in combination with head movement, gaze direction, gain fields, or the like, is used for various purposes, such as the control of a neural prosthetic. In an alternate embodiment, a direct and/or indirect measurement of eye movement, either alone or in combination with head movement, gaze direction, gain fields, or the like, is combined with a measurement of neural activity relating to one or more motor, cognitive, or other functions to enhance and/or refine the control, operation, efficiency and/or accuracy of a neural prosthetic. Measurements pertaining to an array of motor, cognitive, or other functions may be so combined, in connection with alternate embodiments of the present invention, as will be readily appreciated by those of skill in the art. While not wishing to be bound by any particular theory, it is believed that such a combination of measurements more closely mimics the neural processing involved in brain control of normal motor function.

Measurement of motor, cognitive, or other functions can be accomplished in any number of ways, such as by measurement of spiking and/or LFP in corresponding areas of the brain. For example, U.S. Pat. No. 6,952,687 and U.S. patent application Ser. No. 11/086,534 each describe techniques for the measurement of cognitive control signals that are suitable for use in connection with various embodiments of the present invention. Each of these references is incorporated herein in their entirety as though fully set forth.

Therefore, according to a first aspect, a method to control spatial positioning of a prosthetic device of a subject is disclosed, where the prosthetic device is able to assume multiple spatial positions upon input from the subject.

The method comprises: directly or indirectly recording eye position of the subject to produce an eye position signal; recording neural activity relating to a motor, cognitive and/or other function of the subject to produce a neural activity signal; combining the eye position signal and the neural activity signal to provide a recorded behavioral pattern; comparing the recorded behavioral pattern with at least one predetermined behavioral pattern to identify a matching predetermined behavioral pattern, the at least one predetermined behavioral pattern associated with at least one predetermined spatial position of the prosthetic device; and positioning the prosthetic device in the spatial position associated with the matching predetermined behavioral pattern.

In an alternative embodiment, the method comprises: directly and/or indirectly recording eye position of the subject to produce an eye position signal; comparing the eye position signal with at least one predetermined eye position signal to identify a matching predetermined eye position signal, the at least one predetermined eye position signal associated with at least one predetermined spatial position of the prosthetic device; and positioning the prosthetic device in the spatial position associated with the matching predetermined eye position signal.

Recording eye position can in particular be performed by any of the aforementioned techniques, whether direct or indirect. Recording neural activity can similarly be performed by any of the aforementioned techniques, such as by detecting spike activity and/or LFP activity. In particular, the neural activity signal can be the spike rate and/or the LFP spectrum. In certain embodiments, the LFP activity recorded can be in the 25-35 Hz frequency band, although other frequency bands may be suitable for use in connection with alternate embodiments of the present invention. In one embodiment, the neural activity signal results from combining a separately recorded LFP spectrum and spike rate. According to a different aspect, methods to control spatial positioning of the prosthetic device can be performed by detecting the eye position and/or neural activity only.

According to a further aspect, the invention includes a prosthetic device that is able to assume a spatial position on input of a subject. The prosthetic device comprises: means for directly and/or indirectly recording eye position of the subject to produce an eye position signal; means for recording a neural activity related to motor, cognitive and/or another function of the subject to produce a neural activity signal; means for combining the eye position signal and the neural activity signal to produce a recorded behavioral pattern; means for storing at least one predetermined behavioral pattern, the at least one predetermined behavioral pattern associated with at least one spatial positioning of the prosthetic device; means for comparing the recorded behavioral pattern and the at least one predetermined behavioral pattern to identify a matching predetermined behavioral pattern; and means for positioning the prosthetic device in a spatial position associated with the matching predetermined behavioral pattern.

In an alternate aspect, the invention includes a prosthetic device able to assume a spatial position on input of a subject, in which the prosthetic device includes: means for directly and/or indirectly recording eye position of the subject to produce an eye position signal; means for comparing the eye position signal with at least one predetermined eye position signal to identify a matching predetermined eye position signal, the at least one predetermined eye position signal associated with at least one predetermined spatial position of the prosthetic device; and means for positioning the prosthetic device in a spatial position associated with the matching predetermined eye position signal.

The means for recording eye position, for recording neural activity, for producing the recorded behavioral pattern, for storing the behavioral pattern, for comparing the recorded and predetermined behavioral patterns, and for positioning the prosthetic device may all be in electronic communication with one another through any convenient configuration (whether hard-wired, wireless, or any combination thereof), as will be readily appreciated by those of skill in the art.

There are many devices and techniques that may be used for recording eye position and neural activity, as described above.

Similarly, a recorded behavioral pattern may be produced through the use of a component that combines the eye position and neural activity signals and implements a computational model and/or software algorithm to generate a behavioral pattern.

The behavioral pattern may be stored in any number of conventional electronic media, such as a hard disk drive (HDD), a compact disc (CD), a server (whether locally or remotely accessed), or any other conventional storage mechanism that enables the storage of electronic content, whether fixed in the device of the present invention or removable therefrom. Moreover, the format in which the behavioral pattern is stored may vary depending upon the particular features and intended use of the inventive device. For instance, behavioral patterns may be stored in one or more databases, the architecture of which may very depending upon the computational features of the system. Variations will be apparent to those of skill in the art, and can be optimized to account for parameters such as system efficiency, storage capacity, and the like.

Recorded and predetermined behavioral patterns may be compared with a processor that has instructions to perform one or more particular comparative tasks. These tasks may take the form of computer algorithms (e.g., described in software) that are configured to recognize pattern similarities between and among behavioral patterns. Hash tables, machine-learning algorithms, and other commonly used techniques may be readily implemented with a processor to achieve the goals of this feature of the invention. By way of example, U.S. Pat. No. 6,952,687 describes a cognitive state machine configured to implement this type of process, and the methods and systems described therein may be readily used in connection with the present invention.

Control systems for positioning a neural prosthetic device are known in the art, and any such system can be configured for use in connection with alternate embodiments of the present invention.

Further system components may also be included or integrated with the enumerated components, such as, for example, additional processors, a monitor, other peripheral devices, or like system components standard for devices of this type.

According to a further aspect, a method and system are provided to investigate neural basis of a natural behavior in subjects, comprising combining a behavioral task that simulates natural behavior in a laboratory setting with recordings of eye movements and/or neural activity related to motor, cognitive and/or another function of the subject. In the method at least one subject is employed. The subject may be subjected to a behavioral task designed to simulate the natural behavior of interest. The behavior of the at least one subject during the behavioral task may be recorded, as well as the eye movement and/or a neural activity related to motor, cognitive and/or another function of the subject. The recorded behavior, the recorded eye movement and the recorded neural activity (in those embodiments in which neural activity is recorded) are then combined to identify a pattern of recorded eye movement and/or neural activity characterizing the natural behavior.

In some embodiments, the task is designed to reduce the instructions given to the subject letting the subject choose both where to look and where to reach. In those embodiments a pattern of behavior emerges naturally as each animal learns a strategy for earning rewards most easily. The strategies shown by the subject in those embodiments are not completely idiosyncratic and contain common elements.

In one embodiment of the present invention, the aforementioned method for investigating a neural basis of a natural behavior in subjects is used as a "training" process for a neural prosthetic device. In that regard, the training process is implemented with respect to the subject user of a neural prosthetic such that recorded eye movements, neural activity, and/or behaviors relate directly to the user, and can therefore be used to calibrate the device. In alternate embodiments of the present invention, similar information collected from training processes with one or more other subjects can be used to calibrate the device for a user that has not participated in the training process. This may be particularly advantageous in those instances where the ultimate user of a neural prosthetic is clinically incapable of participating in the training process, due to, for example, paralysis or severely compromised brain function; either or both of which the inventive neural prosthetic is designed to address.

The strong parallels existing between the results described herein and work in behavioral game theory on human decision making which aims to understand human behavior in, for example, markets and auctions using lab experiments (C. F. Camerer, *Behavioral came theory: Experiments in strategic interaction*, Princeton University Press, Princeton (2003)) allow extension of results in humans.

Additional embodiments of the methods and systems can be envisioned by a person skilled in the art upon reading of the present disclosure and in particular the Examples section and will not be further described in details.

The following examples are provided to describe the invention in further detail. These examples, which set forth a preferred mode presently contemplated for carrying out the invention, are intended to illustrate and not to limit the invention.

EXAMPLES

The database for the experimental procedure illustrated in the examples contained 44 behavioral recordings (35 from monkey 1; 9 from monkey 2), 549 cell recordings (431 from monkey 1; 118 from monkey 2) and 1282 field recordings (914 from monkey 1; 368 from monkey 2).

Example 1

Predicting Decisions from Eye Movements

To test eye movements and the neural basis of decision-making under more natural conditions, monkeys were trained to perform a free choice task involving a reach search between three targets. In particular, two male rhesus monkeys (*Macaca Mulatta*) participated in the experiments.
Experimental Preparation Each animal was first implanted with a head cap and eye coil under general anesthesia. In a second surgery 64 microelectrodes (2×32 electrode arrays) were chronically implanted in the medial intraparietal area (area MIP), part of PRR, in the posterior parietal cortex of each animal. Structural magnetic resonance imaging was used to identify position and orientation of the IPS and plan the entry point of the electrode array on the cortical surface. Final placement of electrode arrays was determined visually during surgery after resecting the dura and exposing the IPS, parieto-occipital sulcus and post-central dimple. Implantation coordinates for the arrays were 6P,8L and 2P,12L, 4.5 mm below the cortical surface. Coordinates were determined using an electrode manipulator mounted on a stereotaxic instrument (Kopf Instruments, Tujunga, Calif.). Electrode arrays used sharp tungsten microelectrodes (Impedance 300 kf)) arranged in 4 rows of 8 electrodes spaced by 400 pm (MicroProbe, Inc., Potomac, Md.). An additional low impedance ground electrode was placed at each end of each array. Full details of surgical procedures have been previously published (H. Scherberger et al., *Magnetic resonance image-guided implantation of chronic recording electrodes in the macaque intraparietal sulcus, J. Neurosci. Methods,* 130:1-8 (2003)). All surgical and animal care procedures were done in accordance with National Institute of Health guidelines and were approved by the California Institute of Technology Animal Care and Use Committee.

During each session multiple channels of neural activity were passed through a headstage (Plexon, Inc., Dallas, Tex.), filtered (1 Hz-10 kHz; custom), amplified (×10,000; TDT Electronics, Gainesville, Fla.), digitized (20 kHz; National Instruments, TX) and continuously recorded to disk for further analysis (custom C code). The high-pass filter on the TDT amplifier had a significant roll-off resulting in an overall suppression of power below 10 Hz.

Behavioral Task

Each monkey was trained to reach to targets presented on an LCD screen behind a touchscreen (ELO Touchsystems, CA) for juice rewards according to a procedure schematically illustrated in FIG. 1. In a each of a series of trials, monkeys were presented with three visually identical targets on a touchscreen in front of them. The three identical targets were presented on a square grid spaced by 10°. Hand position at the start of the trial was at the center of the screen. One target only contained a reward when touched and rewards were assigned in each trial with equal probability. The monkeys made reaches to targets until they earned the reward. The eyes were free to move and monitored using either a sceral search coil (CNC Engineering, Seattle, Wash.) or, occasionally, an infrared video tracking system (Iscan Inc., Cambridge, Mass.).

In particular, the monkey started each trial by touching a green dot at the center of the screen. After a baseline hold period (1000-1200 ms), the three visually-identical targets were presented on a 3×3 grid (spaced 10°) of eight possible locations around the start point. After a hold period (750-1000 ms) the monkey was allowed to reach to one of the three targets. Only one of the three targets triggered a juice reward when touched. If the monkey did not reach to the target that gave the reward, he was allowed to make additional reaches to targets following subsequent hold periods (500-750 ms). Additional reaches were permitted until the monkey received the reward. Targets were extinguished once they were touched. A different set of three targets from the eight possible locations appeared each trial and the target that gave the reward was chosen from these three targets with equal probability. This stimulus-reward configuration set ensured the monkey didn't repeatedly emit the same stereotyped sequence of movements. Reducing instructions the animal had to follow by allowing him to choose where to look and reach allowed us to simulate more natural behavior in a laboratory setting. In support of this, each animal required relatively little training (1-2 weeks daily following initial chair training) before being proficient (>90% correct) at the task. The timing of the behavioral events registered during performance of the above behavioral task is illustrated on FIG. 2.

The registered reach choices, support the conclusion that each monkey had a strategy for choosing which target to reach to first. Each strategy was characterized by calculating the probability of reaching to a given target first. Other factors, such as hand used, were held constant, and the strategies were learned over several weeks after which time they became fairly stable.

Eye Movements Analysis

The strategies developed by the monkeys to reach the target and a possible predictive role of eye position was analyzed according to the experimental approach illustrated in FIGS. 3 to 7.

In a first series of experiments, the probability of choosing each target for the first reach by the two monkeys according to target position with respect to the initial hand position (H) was tested. In particular, the probability of reaching to a target was estimated by dividing the number of trials a target was chosen first, by the number of trials that target was illuminated.

The results, illustrated in FIG. 3, show a common preference for choosing ipsilateral targets closer to the initial hand position, since both monkeys chose targets that were closer to the central start point more often than targets that were further away (monkey 1 made reaches with his right hand and chose rightward targets with greater probability and monkey 2 made reaches with the left hand and chose leftward targets) (see FIG. 3). This common preference might be explained in terms of minimizing the amount of physical effort required to get a reward. However, this explanation is reported for explanatory purposes only and must not be intended to limit the purpose of the present disclosure. In two out of three trials animals made additional reaches to get a reward. The arrangement of targets around the starting hand position coupled with biases in the first reach choice resulted in the second and third reaches being made in similar directions.

In a second series of experiments, the saccade rate for a sample behavioral session aligned to target onset was tested. Saccades were detected from eye position by smoothly estimating eye velocity and thresholding at 50°/s. Saccade rate was estimated by counting the number of saccades that occurred in non-overlapping 50 ms windows throughout the trial. Trials were averaged aligned either to target onset or to the end of the first reach. The scan stage was 200-700 ms following target onset. The look-reach stage was 300 ms before to 200 ms following reach start.

Figure 4:
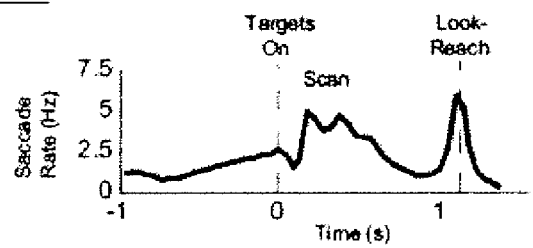
FIG. 4 shows a diagram reporting the saccade rate for a sample behavioral session aligned to target onset in accordance with an embodiment of the invention. The x-axis shows the time in seconds; the y-axis shows the saccade rate in Hertz.

The results illustrated in FIG. 4 show a striking pattern of hand-eye coordination emerging as each monkey selected and executed the first reach. Plotting the saccade rate during the trial revealed hand-eye coordination was organized into distinct stages, and in particular in the scan stage and look-reach stage (FIG. 4).

The scan stage occurs after the targets are presented. During this scan stage, the monkeys looked at the targets. In the scan stage, the saccade rate dipped before rising dramatically to a maximum of five saccades per second (FIG. 4). The initial dip in saccade rate resulted from a change in the inter-saccadic interval distribution that was time-locked to the onset of the targets. This change has also been observed in humans (G. Ariff et al., *A real-time state predictor in motor control: Study* of saccadic eye movements during unseen reaching movements, J. Neurosci., 22:7721-7729 (2002)).

One possible explanation for the saccade rate dip of the scan stage is that ongoing saccade plans were cancelled and restarted to reflect new target locations. This explanation is indicated for explanatory purposes only and not intended to limit the scope of the present disclosure.

The look-reach stage occurs after the scan stage. During the look-reach stage the monkeys looked at the target and then reached to the target. In the look-reach stage the saccade rate dropped to a minimum and then rose sharply as the monkeys made a coordinated hand-eye movement to the chosen target (FIG. 4).

In a third series of the experiments, the eye position was tested during the scan and the look-reach periods in trials where two targets were present and one or other was chosen.

Figure 5:
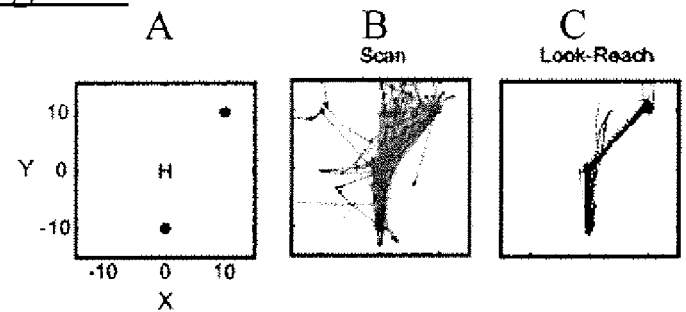
FIG. 5 shows a diagrammatic representation of the eye position in a trial where two targets were present and one or the other was chosen in accordance with an embodiment of the invention. Panel A shows location of the two targets on a bi-dimensional plane with respect to the initial hand position (H); Panel B shows the eye position traces during the scan stage; and Panel C shows the eye position traces during the look-reach stage; traces are shaded according to which target was chosen.

The results illustrated in FIG. 5 show that the end-points of the saccades contained information about the decision-making process. In particular, a saccade made to the target of the reach was registered during the look-reach stage. However, saccades made during the scan stage before this eye position indicated the target to be chosen despite the presence of intervening saccades to other targets. This pattern was present across the database.

In a further series of experiments, the pattern detected in outcome of the experiments illustrated in FIG. 5, was quantified by calculating a viewing fraction during the scan period before the first reach and averaging the viewing fraction across trials when the monkey chose one target or the other. The viewing fraction was estimated by calculating the fraction of time eye position was within a 5° window of given target in a 200 ms window. According to this approach, the target in the pair that the monkey chose more often was identified as the preferred target, and the other target as the non-preferred target. The time axis for all analysis windows was aligned to the center of the window.

Figure 6:
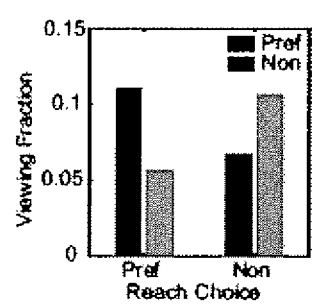
FIG. 6 shows a histogram illustrating the viewing fraction to the preferred (black bars) and non-preferred (white bars) target when the first reach was to the preferred and non-preferred target averaged over all pairs in accordance with an embodiment of the invention. The x-axis shows the reach choice; the y-axis shows the viewing fraction.

The results illustrated in FIG. 6 show a viewing fraction greater for the preferred target than for the non-preferred target when the monkey chose the preferred target, and vice versa when the monkey chose the non-preferred target (FIG. 6).

Additionally, while eye movements before the first reach tended to be made toward the target to be chosen, eye movements later in the trial were different. Specifically, in one animal, eye movements between the first and second reach were made to the target that would not be chosen next. This indicates eye movements were not only made for movement preparation but also reflected a more abstract process related to decision-making.

In an additional series of experiments, the viewing fraction for each target was converted into a single viewing index for each trial and used this index in a receiver-operating characteristic (ROC) analysis, to measure how much information eye position contained about the first reach choice over time. The viewing index was computed for two targets by taking the ratio of the difference between viewing fraction of each target to the sum of both viewing fractions. This computation converted the viewing fractions for two targets into a single number suitable for ROC analysis. ROC analysis measures the probability with which an ideal observer could discriminate between two alternatives given a set of observations. This probability, called a choice probability, has found widespread use in psychology and neuroscience. ROC analysis of all data was done on a 200 ms window stepped by 50 ms through the trial before and during the first reach. Using a longer time window of up to 500 ms increased LFP spectrum choice probabilities but obscured the dynamics. The 200 ms window was chosen as it gave reasonable results and matched the inter-saccadic interval allowing analysis with respect to eye position.

Trials for ROC analysis were selected in which the same two targets were present and one was chosen. This procedure averaged over the location of the third target to give more trials for analysis. In some cases enough data was available to select trials in which the same three targets were present. However, this did not significantly change the results indicating the specific location of the third target had little effect on the activity in these data. At least 100 trials were available for ROC analysis in each session. 95% confidence intervals were estimated from the standard error of the mean choice probability. The eye position on a 200 ms interval to match the average fixation interval during the scanning stage was measured and the ROC analysis of viewing index over time aligned to target onset or reach acquire averaged over all behavioral sessions for monkey.

Figure 7:
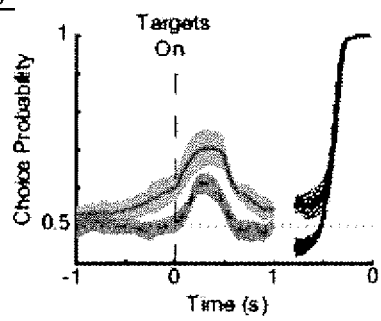
FIG. 7 shows a diagram illustrating the ROC analysis of viewing index over time aligned to target onset or reach acquire averaged over all behavioral sessions for monkey 1 (solid-line curve) and monkey 2 (dashed-line curve) in accordance with an embodiment of the invention.

The results illustrated in FIG. 7 show that the choice probability using eye position was at chance level at the start of the trial and, on average, increased to 0.6 (monkey 1) or 0.7 (monkey 2) 250 ms after the targets came on (FIG. 7). It then decreased before going to 1 at the time of the look and reach. In one animal a significant increase in choice probability was registered before the targets came on. This animal had a tendency to view target locations that he was more likely to choose even before targets were presented.

The above results show that eye position alone can predict reach choices in advance of movement and that eye position is also a useful signal in the study of decision-making.

Example 2

Predicting Decisions from Spiking and LFP Activity

The eye position and spiking and local field potential (LFP) activity was recorded in monkeys during the behavioral task described in Example 1.

In particular a series of experiments was run to see how neural activity developed under the more natural conditions of the reach search task in which the monkeys were free to choose which target to reach to. Since a less-constrained behavior was tested, and there was no guarantee that a certain number of trials would be performed for each trial condition, the neural activity was recorded using chronically implanted microelectrodes. In particular, microelectrode arrays were implanted in the medial intraparietal area (area MIP) of two monkeys and analyzed each signal by predicting which target the animal chose to reach to first. This resulted in very stable recordings and allowed recording more trials from the same population of cells than we could with traditional methods.

Spike events were extracted and classified from the broadband activity using open source (KlustaKwik; available from VA Software through the SourceForge® collaborative development environment) and custom Matlab code (The Mathworks, Natick, Mass.). Usually only one cell was isolated from each electrode.

LFP activity was estimated from broad-band activity by first median filtering the signal with a 1.5 ms filter and then low-pass filtering it at 300 Hz. Median filtering suppressed influence of spiking activity at lower frequencies. Only channels with large amplitude (>4 SD) spiking activity were included in the spike database. All channels were included in LFP database regardless of the presence of spiking activity on that channel. The LFP spectrum characterizes the amount of power in the LFP signal at different frequencies. Analyzing LFP activity according to frequency is important because different information is represented in different frequency bands.

Spike rate and LFP spectrum were estimated on a 200 ms window stepped by 50 ms between estimates. The LFP spectrum was estimated with +/−5 Hz resolution. ROC analysis of spike rate and LFP spectrum was done using these estimates. LFP power in each frequency band was analyzed separately.

The spike rate and LFP spectrum were detected before the first reach for a pair of targets, a preferred target, which had higher overall activity, and a non-preferred target.

Figure 8:
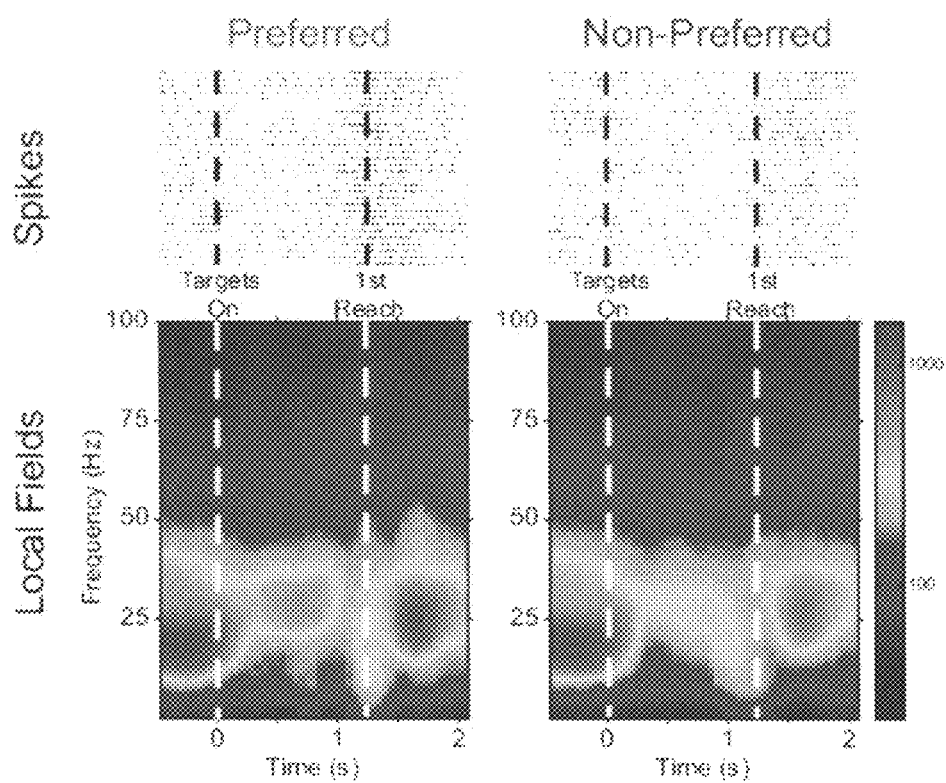
FIG. 8 shows the spike rasters and LFP spectrograms for the preferred and non-preferred directions registered in a monkey subjected to the behavioral task of FIG. 1 before the first reach, in accordance with an embodiment of the invention. Regarding the LFP, the x-axis shows the time expressed in seconds; the y-axis shows the frequency (Hz).
Figure 9:
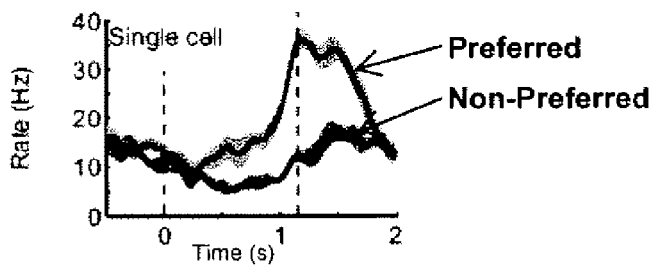
FIG. 9 shows a diagram illustrating the spike rate for the preferred and non-preferred direction registered in a monkey subjected to the behavioral task of FIG. 1 before the first reach in accordance with an embodiment of the invention. The x-axis shows the time expressed in seconds; the y-axis shows the rate in hertz.

The results referred to the spike rate, illustrated in FIG. 8 show that the spike rate built up to a maximum during the reach to the preferred target (FIG. 8), while before the reach to the non-preferred target, this buildup was not present, and the rate was even suppressed (FIG. 8). Additionally, spike rates started to show spatial tuning to the target of a reach movement slowly after the onset of the targets (FIG. 9).

The results illustrated in FIG. 8 show that LFP spectrum revealed complex dynamics at different frequencies. At the start of the trial, there was a peak in the spectrum in a 20 Hz frequency band. After target onset, power in this band was suppressed and the spectral peak shifted to a higher frequency 25-35 Hz band. At the time of the reach, this power was suppressed and activity shifted to a lower frequency 1-10 Hz band. A similar pattern could be seen for reaches to the preferred and non-preferred targets. The LFP spectrum also showed spatial tuning to the target of a reach movement, the spatial tuning developing immediately after the onset of the target.

Figure 10:
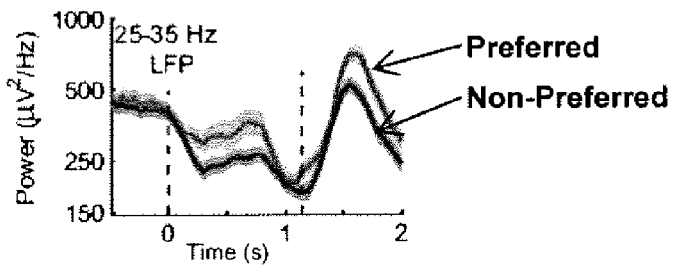
FIG. 10 shows a diagram illustrating the 25-35 Hz LFP power for the preferred and non-preferred directions registered in a monkey subjected to the behavioral task of FIG. 1 before the first reach in accordance with an embodiment of the invention. The x-axis shows the time expressed in seconds; the y-axis shows the LFP power expressed as $\mu V^2/Hz$.
Figure 11:
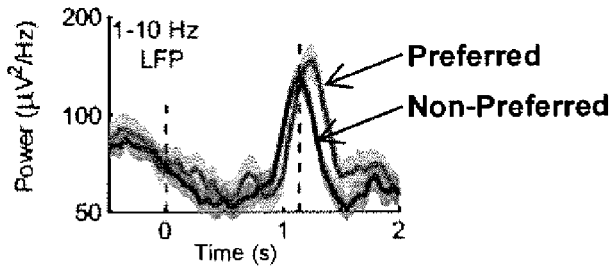
FIG. 11 shows a diagram illustrating the 1-10 Hz LFP power for the preferred and non-preferred directions registered in a monkey subjected to the behavioral task of FIG. 1 before the first reach in accordance with an embodiment of the invention. The x-axis shows the time expressed in seconds; the y-axis shows the LFP power expressed as $\mu V^2/Hz$.

In particular, results illustrated in FIGS. 10 and 11 show a different spatial tuning of the power to the target in the spectrum. Power in the 25-35 Hz frequency band was spatially tuned after target onset through the reach. This tuning was absent during the reach tuning but it returned after the reach. The 1-10 Hz frequency band only showed spatial tuning during the reach with an increase in activity for reaches to one direction before reaches to the other. Across the database, 86% of cells (422 of 549), 62% (794 of 1282) of 2535 Hz LFP recordings and 93% (1192 of 1282) of 1-10 Hz LFP recordings showed significant ($p<0.01$; ANOVA) spatially tuned activity during the task.

A comparison of the relative timing of spatial tuning in spiking and LFP activity for these recordings with significant activity, suggested that 25-35 Hz LFP activity became tuned earliest, followed by spike activity and then by 1-10 Hz LFP activity.

In view of the difficulties in directly comparing the strength of spike rates and LFP power quantitatively due to the statistically different nature of these observations. Spiking activity is a point process of spike times while LFP activity is a continuous process of voltage fluctuations. A receiver-operating characteristic (ROC) analysis was then used to address this problem. This analysis results in choice probabilities for either spike rate or LFP power that can be directly compared. This makes ROC analysis well suited for the comparison of spike rates and LFP spectra.

The results on a single subject illustrated in FIG. 12 show that analysis of the data on a 200 ms window choice probabilities using LFP power in specific frequency bands were comparable with those based on spike rate but had different time courses during the trial.

A population average supported this result as illustrated in FIG. 13 and in agreement with our earlier analysis (above), LFP power between 25-35 Hz was most strongly tuned early in the trial, increasing quickly to almost 80%.

At the same time in the trial the choice probability using the firing rate of a single cell was much less, typically barely above chance, and did not reach the same level for another 100 ms. Although the latency of the choice probability using spike firing was longer, we found it increased to a maximum during reaching, often at levels of 100% for individual cells. Interestingly, at this time choice probabilities based on 25-35 Hz LFP power had decreased while those based on 1-10 Hz LFP power had increased to approximately the same level as spiking.

Across the population of recordings with spatially-tuned activity this progression could also be seen examining the number of recordings with choice probabilities greater than 0.6. At 300 ms after target onset, 23% (97 of 422) cell recordings, 70% (555 of 794) of 25-35 Hz LFP recordings, and 12% (143 of 1192) of 1-10 Hz LFP recordings had choice probability greater than 0.6. In contrast, during reaching 86% (363 of 422) cell recordings, 6% (48 of 794) 25-35 Hz LFP recordings, and 86% (1025 of 1192) 1-10 Hz LFP recordings had choice probability greater than 0.6. Since these comparisons were done based on choice probabilities, which have a common scale, the differences do not result from a normalization bias. Instead, they result from a difference in the timing of how information is represented in each signal.

While previous work shows spiking and LFP activity are coherent in some frequency bands, these results show that spiking and LFP activity can also be dissociated. This is similar to results in V1 during visual stimulation (N. K. Logothetis et al., *Functional imaging of the monkey brain*, Nat. Neurosci., 2:555-62. (1999)). Specifically, the LFP activity was found in a 25-35 Hz frequency band predicts reach choices before spiking. This result could be due to a combination of factors such as a bias in the cell population our recordings sampled and how activity is organized in the neuronal network.

The finding of a lack of tuning for eye position in the 25-35 Hz LFP activity is in counter-distinction to the strong tuning of spiking activity by eye position. In PRR (which overlaps MIP) this tuning results both from the retinotopic coding of response fields and direct eye position modulation of these response fields.

The fact that these eye position effects do not appear to be present in MIP may reflect a lack of columnar organization for eye position. Alternatively, early LFP activity may be due to top-down inputs to the area coming from reaching areas in the frontal lobe because activity in these areas does not depend strongly on eye position (Cisek, P. & Kalaska, J. F., *Modest gaze-related discharge modulation in monkey dorsal premotor cortex during a reaching task performed with free fixation*, J. Neurophysiol., 88:1064-1072 (2002)). Spiking may instead reflect outputs of the area. The presence of top-down inputs from frontal cortex to parietal cortex during free choice would have important implications for how information is processed in frontal-parietal networks. These explanations are indicated for explanatory purposes only and not intended to limit the scope of the present disclosure.

Example 3

Predicting Decisions by Combining Eye Position with Neural Activity

To investigate whether combining eye position with neural activity improves our ability to predict decisions for reaches and improve the control of a neural prosthetic, a further series of experiments was carried out.

To see whether combining eye position with neural activity would improve reach choice predictions, the choice probability using an operating-characteristic (OC) analysis. OC analysis measures the probability with which an observer can discriminate between two alternatives given a set of simultaneously recorded signals (R. O. Duda et al., *Pattern Classification*, 2nd Edition. New York: John Wiley and Sons (2001)).

OC analysis of combined eye position and neural activity was done using the viewing index, firing rate and spectral estimates used for the ROC analysis. OC analysis was performed by first ranking both viewing index and neural activity estimates across trials for a pair of targets. A threshold was then chosen for both quantities and a hit rate and false positive rate were computed for the threshold pair. This was repeated for different values of the threshold. An OC curve was generated by using the minimum false positive rate for a given hit rate. The choice probability was the area under this curve. To test whether the performance improvement of OC analysis of two variables was significantly better than ROC analysis of each variable alone, the data were shuffled and estimated how much OC analysis of the shuffled data improved compared with ROC analysis of the same data.

This is similar to the ROC analysis used above for eye position, spike and LFP activity individually in the experiments of Examples 1 and 2, but extends it to multiple signals.

Figure 14:
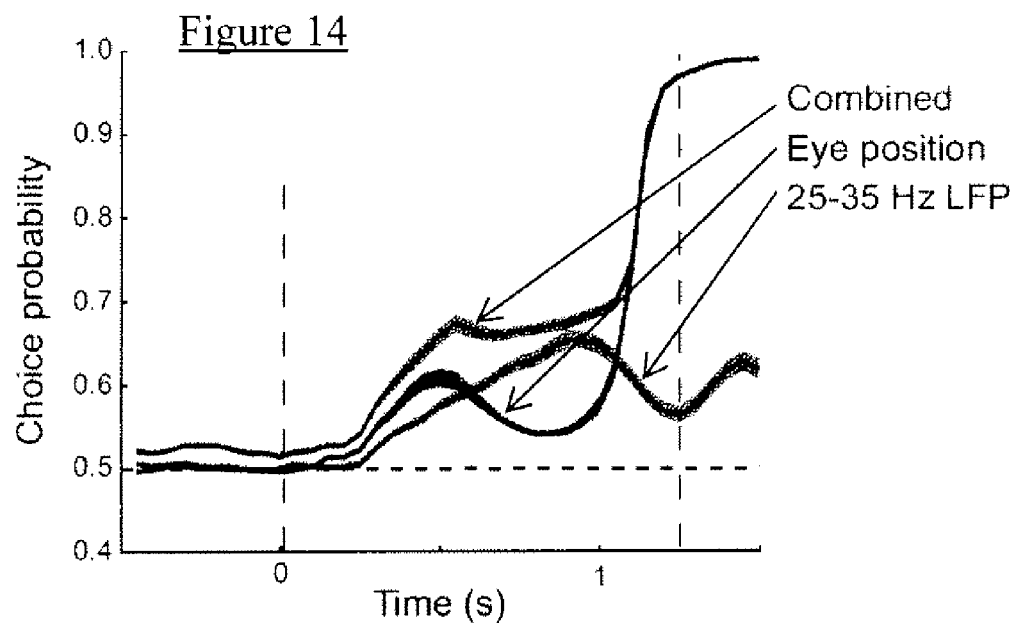
FIG. 14 shows a diagram illustrating a comparison of population average choice probabilities from ROC analysis using eye position and 25-35 Hz LFP activity in accordance with an embodiment of the invention. Population average ROC analysis of eye position activity, 25-35 Hz LFP activity and OC analysis of eye position and 25-35 HZ LFP activity combined. The x-axis shows the time expressed in seconds; the y-axis shows the choice probability.

The results illustrated in FIG. 14 show that a comparison of choice probability from an OC analysis combining eye position and 25-35 Hz LFP activity with choice probability from an ROC analysis of eye position and 25-35 Hz LFP activity, improved predictions.

These results indicate eye position and LFP activity contain complementary not redundant information about decision-making.

Since according to the experimental procedures herein exemplified, eye position predicted reach choice perfectly at the time of the look reach, the choice probabilities earlier during the scan stage were further tested.

Figure 15:
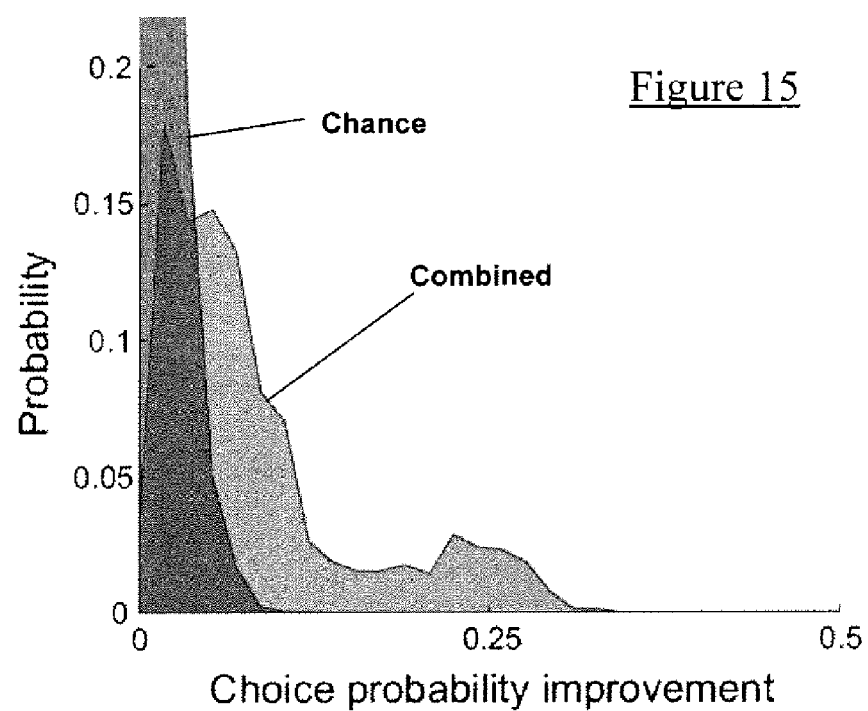
FIG. 15 shows a diagram illustrating the difference between choice probabilities during the scan stage with eye position and 25-35 Hz LFP activity combined and with 25-35 Hz LFP activity alone and difference expected by chance in accordance with an embodiment of the invention. The x-axis shows the time expressed in seconds; the y-axis shows the probability.

The results illustrated in FIG. 15 show that during this stage combining eye position and 25-35 Hz LFP activity improves choice probabilities compared with using either signal alone. In particular, choice probabilities during the scan stage immediately after target onset could improve by more than 25%. Similar results were obtained using spiking activity. Since OC analysis uses more information more flexibly than ROC analysis (see Methods) we would expect an improvement in choice probabilities using this technique by chance alone. To test whether the observed choice probability improvements could be explained by chance eye position and LFP activity were shuffled across all trials, the degree of improvement for each session estimated and the distribution plotted (FIG. 15). The median choice probability improved by only 1.7% and the maximum by only 8% indicating the choice probability improvements we observed were highly significant ($p<0.001$).

Example 4

Eye Position Tuning of LFP Plan Activity

The results of the ROC analysis also showed that eye position and LFP power choice probabilities increase with similar latencies after the onset of the targets while those based on spiking activity have longer latency.

A possible explanation of these differences can be that spiking and LFP activity have different biophysical sources: Recorded spiking activity is biased toward the action potentials of larger neurons that are more likely to be the outputs of an area while LFP activity reflects synaptic activity resulting from inputs to the area and local processing. Differences in the choice probability time course of these signals may be a consequence of these different biophysical sources and how activity is organized in the neuronal network. Since neural activity in some brain areas depends on eye position more than in others we reasoned that studying the dependence of LFP activity on eye position would help answer this question by teasing apart potential network sources of this signal. For example, spiking activity in PRR, a likely site of our recordings, represents reach plans in an eye-centered reference frame (A. P. Batista et al., *Reach plans in eye centered coordinates*, Science, 285:257-260 (1999)). Spiking activity in eye movement area LIP also has heavy projections to the site of the recordings (Lewis, J. W. & Van Essen, D. C., *Corticocortical connections of visual, sensorimotor, and multimodal processing areas in the parietal lobe of the macaque monkey*, J. Comp. Neurol., 428:112-137 (2000)). In contrast, spiking activity in dorsal premotor cortex, which also projects to the site of our recordings (P. B. Johnson et al., *Cortical networks for visual reaching: physiological and anatomical organization of frontal and parietal lobe arm regions*, Cereb. Cortex, 6:102-19. (1996)), depends much less on eye position (Cisek, P. & Kalaska, J. F., *Modest gaze-related discharge modulation in monkey dorsal premotor cortex during a reaching task performed with free fixation*, J. Neurophysiol., 88:1064-1072 (2002)). Therefore, whether or not LFP activity that is spatially tuned during the reach plan (LFP reach plan activity) depends on eye position has network implications.

Two methods were used to determine whether 25-35 Hz LFP reach plan activity depends on eye position. First, we tested whether there was a difference in LFP power for two different eye positions given the same reach choice. Only 29 of 794 sessions had a difference in their mean LFP activity ($p<0.05$; t-test). This was not significant (permutation test: $p>0.05$). The relationship between LFP reach plan activity and eye position were changed by shuffling eye position across trials with the same reach choice and repeated the OC analysis presented above, whereas shuffling should reduce the choice probability if LFP reach plan activity depends on eye position.

Figure 16:
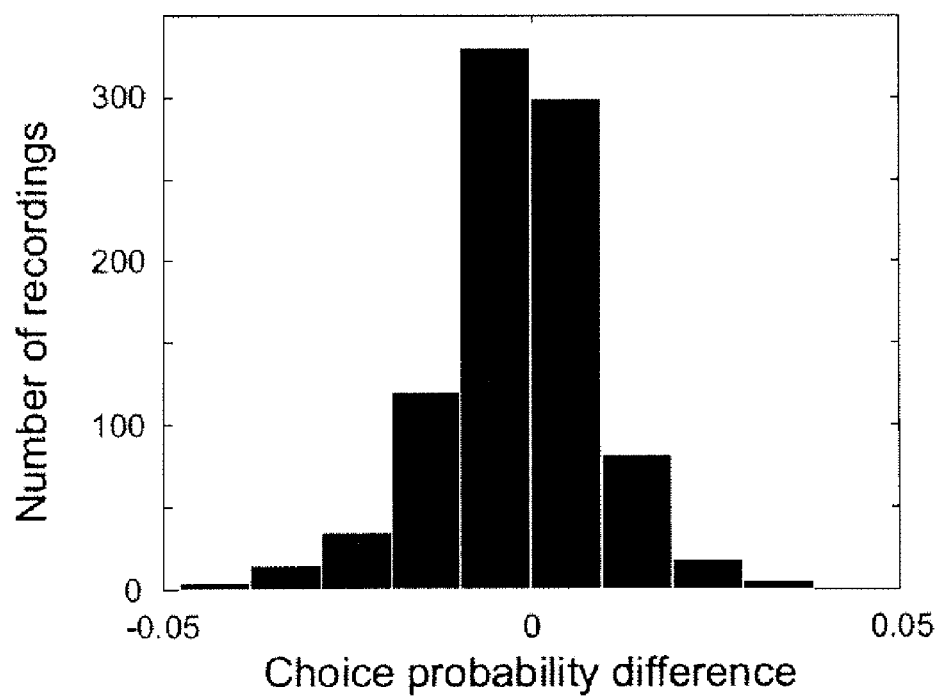
FIG. 16 shows a histogram illustrating the distribution of difference in choice probability for OC analysis using 25-35 Hz LFP activity with and without shuffling eye position in accordance with an embodiment of the invention. The x-axis shows the choice probability difference; the y-axis shows number of recordings.

The results illustrated in FIG. 16 show that distribution of choice probabilities when eye position was shuffled was not different than when the relationship between eye position and the 25-35 Hz LFP reach plan activity was preserved (FIG. 16; $p=0.85$ KS-test). Therefore, LFP reach plan activity does not depend on eye position.

The results illustrated in the examples above support the conclusion that before the first reach, eye position is predictive of reach choices when the subject scans the targets. These results therefore indicate eye movements participate in the reach selection process and support a method for improving performance of neural prosthetics for paralyzed patients that can still make eye movements.

The experimental procedures illustrated in the examples also support the conclusion that recorded spiking and LFP activity represent specific yet different aspects of cognitive processing. In particular, LFP and spiking activity can be dissociated and are both predictive of reach choices with LFP activity predicting reach choices before spiking. The above results therefore provide inter alia an approach to investigating multiple area spike-field recordings to understand the interactions of neural activity across frontal-parietal networks.

Also since scanning eye movements predict reach choices earliest, followed by LFP activity and spiking activity in the medial intraparietal area (area MIP) combining eye position information and neural activity improved reach choice predictions early on.

In particular, the above results show that natural, unconstrained hand-eye coordination contains a great deal of information about both cognitive variables like decisions for plans during a scan stage and motor variables like movement direction during a look-reach stage. Accordingly combining eye position information and neural activity can be used in methods for improving performance of neural prosthetics for paralyzed patients that can still make eye movements included in the scope of the claims.

In particular, methods and prosthetic devices can be designed to record eye position directly during prosthetic control and combine this information with simultaneously recorded neural activity to improve predictions.

Otherwise, a method or prosthetic device does not require direct measurement of eye position. Instead it involves treating it as an unobserved variable whose value can be inferred from neural recordings and behavioral recordings in the past. Neural recordings to infer eye position could be made from eye movement areas directly or from areas involved in coordinating the eye with other systems.

In either case, the above mentioned results suggest ways the architecture of neural prosthetic decoding schemes can be modified to improve system performance by including eye position information While the methods and systems have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the claims.

What is claimed is:

1. A prosthetic device able to assume a spatial position on input of a subject, the prosthetic device comprising:
    means for recording eye position information of the subject to produce an eye position signal;
    means for recording a neural activity of the subject to produce a neural activity signal;
    means for storing at least one predetermined behavioral pattern, the at least one predetermined behavioral pattern associated with at least one spatial positioning of the prosthetic device;
    processing means coupled to the means for recording eye position information, the means for recording a neural activity and the means for storing, the processing means receiving an eye position signal from the means for recording eye position information during a scan stage occurring after the subject views a plurality of reach goals but before the subject selects one of the plurality of reach goals, receiving a neural activity signal from the means for recording a neural activity signal during neural activity occurring during the scan stage, combining the eye position signal and neural activity signal recorded only during the scan stage to produce a recorded behavioral pattern, predicting a selection of one of a plurality of reach goals by comparing the recorded behavioral pattern and the at least one predetermined behavioral pattern to identify a matching predetermined behavioral pattern, the recorded behavioral pattern associated with a selection of one of the plurality of reach goals after the scan stage, and outputting a spatial position control signal associated with the matching predetermined behavioral pattern; and
    means for positioning the prosthetic device coupled to the processing means to receive the spatial position control signal and position the prosthetic device in a spatial position associated with the matching predetermined behavioral pattern.

2. The prosthetic device of claim 1, wherein the means for recording eye position is configured to record eye position directly.

3. The prosthetic device of claim 1, wherein the means for recording eye position is configured to record eye position indirectly.

4. The prosthetic device of claim 1, wherein the means for recording the neural activity is configured to detect spike activity, local field potential (LFP) activity, or both.

5. The prosthetic device of claim 1, wherein the subject is a primate.

6. A prosthetic device able to assume a spatial position on input of a subject, the prosthetic device comprising:
    an eye position recorder to produce an eye position signal;
    a neural activity recorder to produce a neural activity signal;
    a storage mechanism to store at least one predetermined behavioral pattern, the at least one predetermined behavioral pattern comprising at least one predetermined eye position signal associated with at least one spatial positioning of the prosthetic device;
    a processor coupled to the eye position recorder, the neural activity recorder, and the storage mechanism, the processor receiving an eye position signal from the eye position recorder during a scan stage occurring after the subject views a plurality of reach goals but before the subject selects one of the plurality of reach goals, receiving a neural activity signal from the neural activity recorder during neural activity occurring during the scan stage, combining the eye position signal and neural activity signal recorded only during the scan stage to produce a recorded behavioral pattern, predicting a selection of one of a plurality of reach goals by comparing the recorded behavioral pattern and the at least one predetermined behavioral pattern to identify a matching predetermined behavioral pattern, the recorded behavioral pattern associated with a selection of one of the plurality of reach goals after the scan stage and outputting a spatial position control signal associated with the matching predetermined behavioral pattern; and
    a control system coupled to the processor to receive the spatial position control signal and to position the prosthetic device in a spatial position associated with the matching predetermined behavioral pattern.

7. The prosthetic device of claim 6, wherein the eye position recorder is configured to record eye position directly.

8. The prosthetic device of claim 6, wherein the eye position recorder is configured to record eye position indirectly.

9. The prosthetic device of claim 6, wherein the neural activity recorder is configured to detect spike activity, local field potential (LFP) activity, or both.

10. The prosthetic device of claim 6, wherein the subject is a primate.

11. A prosthetic device able to assume a spatial position on input of a subject, the prosthetic device comprising:
    means for recording an eye position of the subject to produce an eye position signal;
    processing means coupled to the means for recording, the processing means receiving the eye position signal from the means for recording eye position information during a scan stage occurring after the subject views a plurality of reach goals but before the subject selects one of the plurality of reach goals, predicting a selection of one of a plurality of reach goals by comparing a portion of the eye position signal received only during the scan stage with at least one predetermined eye position signal to identify a matching predetermined eye position signal associated with at least one predetermined spatial position of the prosthetic device, the portion of the eye position signal associated with a selection of one of the plurality of reach goals after the scan stage, and outputting a spatial position control signal associated with the predetermined spatial position; and means for positioning coupled to the processing means to receive the spatial position control signal and position the prosthetic device in a spatial position associated with the matching predetermined eye position signal.

12. The prosthetic device of claim 11, wherein the means for recording eye position is configured to record eye position indirectly.

13. The prosthetic device of claim 11, wherein the subject is a primate.

14. A prosthetic device able to assume a spatial position on input of a subject, the prosthetic device comprising:

an eye position recorder to record an eye position of the subject to produce an eye position signal;

a processor coupled to the eye position recorder, the processor receiving the eye position signal from the eye position recorder during a scan stage occurring after the subject views a plurality of reach goals but before the subject selects one of the plurality of reach goals, predicting a selection of one of a plurality of reach goals by comparing a portion of the eye position signal received only during the scan stage with at least one predetermined eye position signal to identify a matching predetermined eye position signal associated with at least one predetermined spatial position of the prosthetic device, the portion of the eye position signal associated with a selection of one of the plurality of reach goals after the scan stage, and outputting a spatial position control signal associated with the predetermined spatial position; and a control system coupled to the processor to receive the spatial position control signal and to position the prosthetic device in a spatial position associated with the matching predetermined eye position signal.

15. The prosthetic device of claim 14, wherein the eye position recorder is configured to record eye position indirectly.

16. The prosthetic device of claim 14, wherein the subject is a primate.

* * * * *